US009636516B2

(12) United States Patent
Schwarz

(10) Patent No.: US 9,636,516 B2
(45) Date of Patent: May 2, 2017

(54) METHODS AND DEVICES FOR TISSUE TREATMENT USING SHOCK WAVES AND ELECTROMAGNETIC FIELD

(71) Applicant: BTL HOLDINGS LIMITED, Limassol (CY)

(72) Inventor: Tomáš Schwarz, Prague (CZ)

(73) Assignee: BTL Holdings Limited, Limassol (CY)

( * ) Notice: Subject to any disclaimer, the term of this patent is extended or adjusted under 35 U.S.C. 154(b) by 0 days.

(21) Appl. No.: 14/870,713

(22) Filed: Sep. 30, 2015

(65) Prior Publication Data

US 2017/0087373 A1    Mar. 30, 2017

(51) Int. Cl.
 *A61H 23/00* (2006.01)
 *A61N 5/06* (2006.01)
 *A61N 2/00* (2006.01)
 *A61N 2/02* (2006.01)
 *A61N 5/067* (2006.01)

(52) U.S. Cl.
 CPC ........... *A61N 2/002* (2013.01); *A61H 23/008* (2013.01); *A61N 2/004* (2013.01); *A61N 2/02* (2013.01); *A61N 5/0625* (2013.01); *A61N 2005/067* (2013.01); *A61N 2005/0659* (2013.01)

(58) Field of Classification Search
 CPC ...... A61H 23/008; A61H 23/02; A61H 1/006; A61H 1/008; A61H 9/0007; A61H 9/005; A61H 9/0071; A61H 15/02; A61B 17/225–17/2017; A61N 5/06–2005/073
 See application file for complete search history.

(56) References Cited

U.S. PATENT DOCUMENTS

| 2004/0073079 A1* | 4/2004 | Altshuler | A61B 5/6843 600/1 |
| 2005/0049543 A1* | 3/2005 | Anderson | A61B 18/14 604/20 |
| 2008/0228520 A1* | 9/2008 | Day | G09B 19/0038 705/2 |
| 2008/0312647 A1* | 12/2008 | Knopp | A61B 18/1477 606/41 |
| 2011/0046523 A1* | 2/2011 | Altshuler | A61N 7/02 601/3 |
| 2012/0029394 A1* | 2/2012 | Babaev | A61B 18/203 601/2 |
| 2012/0150079 A1* | 6/2012 | Rosenberg | A61H 7/003 601/6 |
| 2013/0178764 A1* | 7/2013 | Eckhouse | A61H 7/008 601/2 |
| 2014/0303525 A1* | 10/2014 | Sitharaman | A61N 7/00 601/2 |

(Continued)

OTHER PUBLICATIONS

Gerdesmeyer, L., et al., Radial Extracorporeal Shockwave Therapy (rESWT) in Orthapaedics. J. Minerals. (4 pages) Munich, Germany. 11(4): 36-39; 2004.

*Primary Examiner* — Valerie L Woodward
(74) *Attorney, Agent, or Firm* — Kenneth H. Ohriner; Perkins Coie LLP

(57) ABSTRACT

Devices and methods for tissue treatment produce a shock wave therapy and electromagnetic field therapy. The shock wave therapy provides stimulation of the blood circulation and stimulates the treated cells. The electromagnetic field enables thermal treatment of tissue. Combination of both therapies improves soft tissue treatment, mainly connective tissue in the skin area and fat reduction.

30 Claims, 2 Drawing Sheets

(56) References Cited

U.S. PATENT DOCUMENTS

| | | | |
|---|---|---|---|
| 2014/0350438 A1* | 11/2014 | Papirov | A61B 17/225 601/2 |
| 2015/0141877 A1* | 5/2015 | Feldman | A61N 7/00 601/18 |
| 2015/0165238 A1* | 6/2015 | Slayton | A61B 18/18 601/2 |
| 2016/0016013 A1* | 1/2016 | Capelli | A61N 7/00 601/2 |

* cited by examiner

METHODS AND DEVICES FOR TISSUE TREATMENT USING SHOCK WAVES AND ELECTROMAGNETIC FIELD

FIELD OF THE INVENTION

The invention relates to method and device for soft tissue treatment, mainly connective tissue in the skin area and fat reduction.

BACKGROUND OF THE INVENTION

Human skin is tissue which is commonly treated in order to improve its visual appearance. Skin is composed of three basic elements: the epidermis, the dermis and the hypodermis or so called subcutis. The outer and also thinnest layer of skin is the epidermis. Epidermis contains mainly stratified squamous epithelium of which the outer side keratinizes and ensures coverage whereas the inner side contains a pigment. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT).

SWAT is formed by aggregation of fat cells ranging up to 120 microns in diameter and containing as much as 95% glycerides and fatty acids by volume. Overeating and unhealthy lifestyles may result in an increase of size and/or number of the fat cells. The fat cells create lobules which are bounded by connective tissue, fibrous septa (retinaculum cutis).

Another part of adipose tissue is located in peritoneal cavity and is known as abdominal obesity. Visceral fat layer forming visceral white adipose tissue (VWAT) is located between parietal peritoneum and visceral peritoneum, closely below muscle fibers adjoining the hypodermis layer.

Excess of adipose tissue in subcutaneous or abdominal area may be perceived as aesthetically undesirable, mainly in the buttocks, thighs, abdomen or hips, where even weight loss after dieting and exercise may not lead to satisfactory results. Moreover, in the last few decades, more people suffer from growth of visceral white adipose tissue (VWAT) mainly in their abdominal area. Visceral fat has been also linked to various cardiovascular diseases and diabetes.

The undesirable topographic skin appearance may also be caused by changes in dermal or sub-dermal layer of the skin, especially by excessive number or volume of fat cells, weakening of fibrous septas, loss of elasticity and/or limited lymph flow, which may result in accumulation of toxins.

Shock waves are acoustic waves characterized by steep pressure amplitude growth in comparison to the surrounding pressure. Despite their relationship with other mechanical waves, shock waves are different mainly in pressure magnitude and shape of the pressure wave. In comparison to ultrasound waves where the pressure periodically oscillates with limited bandwidth and amplitude, shock waves are characterized by non-linearity during the wave propagation. In the present invention, shock wave propagation is characterized by swift positive pressure increase in the range from one nanosecond up to 100 microseconds with positive peak pressure amplitudes up to 150 MPa. In comparison, regular ultrasound methods have positive peak pressure amplitudes up to about 3 MPa. The pulse duration (based on the time the pressure exceeds a half value of peak positive pressure) is preferably in the range of hundreds of nanoseconds to 10-100 of microseconds.

There are four main principles for generating shock waves: electrohydraulic, piezoelectric, electromagnetic and ballistic. The shock waves produced by electrohydraulic principle, piezoelectric principle or electromagnetic principle are traditionally used for destruction of calculi e.g. kidney stones. As these shock waves are focused, they may be characterized as hard shock waves because the energy is directed into small point in the tissue.

The ballistic shock waves have a naturally non-focused/radial propagation. Radial/non-focused propagation is characterized by smooth propagation.

Various non-invasive methods for skin treatment containing light, radiofrequency, microwave, and ultrasound treatment has been previously developed. Nevertheless, improved treatments in aesthetic medicine are needed.

SUMMARY OF THE INVENTION

Methods and devices for a non-invasive treatment of soft tissue including SWAT, VWAT and connective tissue use a shock wave therapy and electromagnetic field therapy.

A ballistic mechanism of shock wave generation may be used. The ballistic shock wave mechanism contains a projectile striking against an applicator head for generating the shock wave. The ballistic shock waves have a naturally non-focused, planar or moderately focused propagation. Ballistic shock wave methods of propagation are characterized by smooth propagation. Also other non-focused, radial or moderately focused methods may be used.

The electromagnetic field may be generated by a bipolar, monopolar, unipolar electrodes in direct, indirect or even noncontact arrangement with the skin surface. The electromagnetic field frequency may be in the range from 0.1 MHz to 10 GHz.

The electromagnetic field may be generated by a laser diode module or a LED. The electromagnetic field wavelength may be preferably in the range from 600 nm to 1200 nm.

Combinations of both therapies provide new soft tissue treatment with reduced risk of adverse effects. Treatment may lead to remodeling of a soft tissue in the skin area including white adipose tissue. Remodeling may include reduction in number and/or volume of the visceral white adipose tissue and/or the subcutaneous white adipose tissue. Treatment may also lead to improvement of connective tissue elasticity, mainly elasticity of fibrous septae connecting the dermis to underlying fascia.

Although neocollagenesis is normally induced at temperatures higher than 48° C., the combination of shock wave and electromagnetic field enables improved results at lower temperatures and with less stress of the tissue. Temperature of the soft tissue during the treatment may be about 32-48° C.

According to another embodiment the temperatures may reach above 50° C. which leads to thermal denaturation of collagen and collagen shrinkage.

The sum of the energy flux density of the shock wave and electromagnetic field applied to the patient simultaneously, successively or in overlap is typically above $1~\text{mW}\cdot\text{mm}^{-2}$. With the simultaneous method, EMF and SWT are both used simultaneously during the time interval e.g. 1-10 seconds. In the successive method, EMF is used during a first time interval of e.g., 1-5 seconds. EMF is then stopped and SWT is used in a subsequent time interval of e.g., 6-10 (immediately afterwards the EMF ends, with the combined application time in this example totaling to 10 seconds). In the overlapping method, EMF is used during a first time interval from e.g., 1-7 seconds, and SWT is used in a second overlapping time interval of e.g., 4-10 seconds (wherein during the second time interval the EMF and SWT are simultaneously applied over the second interval starting at 4 seconds and ending at 7 seconds).

In comparison with known techniques, the present device and method enable gentle treatment with no surgery and reduced amounts of energy delivered into the tissue.

The present methods and device may provide improved soft tissue treatment, mainly in skin region such improving skin laxity, skin tightening, wrinkles reduction and including fat cells elimination.

GLOSSARY

"lipolysis" includes apoptosis and/or necrosis of the targeted adipocytes.

"shock wave" is characterized by swift positive pressure increase in the range from ones of nanoseconds up to tens of microseconds with positive peak pressure amplitudes up to 150 MPa. The pulse duration (based on the time the pressure exceeds a peak positive pressure/2) is approximately in the range of hundreds of nanoseconds to tens of microseconds.

"soft tissue remodeling" or "remodeling of soft tissues" means reorganization or renovation of existing tissue with improvement of its elasticity and visual appearance, including reduction of white adipose tissue in number and/or volume.

DETAILED DESCRIPTION

Figure 1:
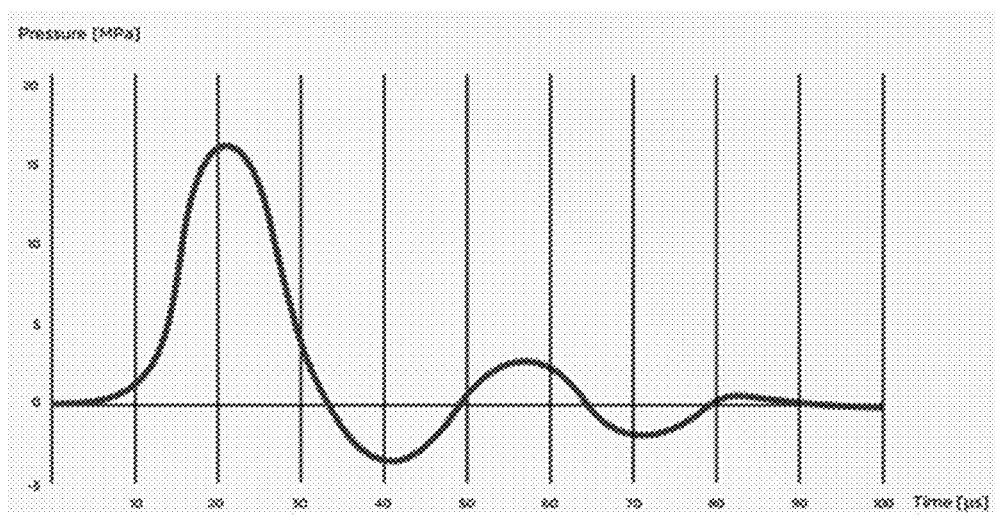
FIG. 1 is an example of shock wave propagation

FIG. 1 shows an example of shock wave propagation. Shock waves are acoustic waves characterized steep pressure amplitude growth in comparison to the surrounding pressure. The shock waves are characterized by non-linearity during the wave propagation. The positive peak pressure is above 0.1 MPa, more preferably 3 MPa, even more preferably at least 7 MPa, most preferably at least 15 MPa. The peak pressure in the positive maximum may be up to 150 MPa. The pulse duration of the shock wave (based on the time the pressure exceeds a half value of peak positive pressure) may be preferably in the range of hundreds of nanoseconds to tens of microseconds.

In comparing mechanical waves e.g. ultrasound and shock waves, not only are there differences in the shape and the propagation, but there are also significant differences between the physical effect of ultrasound and shock waves on the treated tissue, and particularly a cavitation effect. Cavitation is formation of gas bubbles in a fluid environment which occurs during the negative pressure wave in the liquid. Ultrasonic cavitation bubbles represent acoustic inhomogeneity in which incoming acoustic energy is absorbed and dissipated. Due to the high frequency of ultrasound waves, the acoustic energy may lead to rapid growth of cavitation bubbles and later to inertial cavitation effects, with breakup of the bubbles and violent damage of the surrounding tissue. Shock waves can reduce cavitation and the violent break up of cells resulting from cavitation.

The repetition rate of the shock wave may be in the range from 0.1 Hz to 100 Hz, more preferably in the range from 0.5 to 50 Hz, most preferably in the range from 1 Hz to 40 Hz.

Four main principles for generating shock waves are used: electrohydraulic, piezoelectric, electromagnetic and ballistic. The shock waves produced by spark discharge, piezoelectric principle or electromagnetic principle are traditionally used for destruction of calculi e.g. kidney stones and based on its wave propagation it is possible to summarize them as focused. These three methods are also sometimes referred as hard shock waves because the energy is directed into small point in the tissue. On the other hand the electrohydraulic, piezoelectric, electromagnetic principle may be suitable if they are non-focused/radial, planar or moderately focused, and therefore softened.

Ballistic shock waves have a naturally non-focused/radial, planar or moderately focused propagation. Non-focused/radial, planar shock waves are characterized by smooth/soft propagation and therefore are preferred. Ballistic shock waves may be generated by striking of a bullet inside a guiding tube to a percussion guide. The bullet may be accelerated by pressurized gas, electric field, magnetic field or other technique.

Also other principles (e.g. electrohydraulic, piezoelectric and electromagnetic) for generating non-focused, radial or moderately focused shock waves may be used. Moderate focus means varying levels of focused ultrasound energy or focal point in a distance longer than the treated tissue extends, where the energy in the focal point is not sufficient to cause harm of tissue.

In order to achieve the best results in the soft tissue, the energy flux density of the shock waves is preferably in the range between 0.001 mW·mm$^{-2}$ and 160 mW·mm$^{-2}$, more preferably in the range between 0.001 mW·mm$^{-2}$ and 100 mW·mm$^{-2}$, most preferably in the range between 0.001 mW·mm$^{-2}$ and 50 mW·mm$^{-2}$.

Electromagnetic field used for heating the soft tissue may be radiofrequency field or microwave field, typically in the range of 0.1 MHz to 25 GHz, more preferably in the range from 0.1 MHz to 435 MHz, most preferably in the range from 0.1 MHz to 28 MHz. All the above mentioned waves may cause movement of charged particles e.g. ions, rotation of dipolar molecules or polarization of normally non polar particles and therefore increase the tissue temperature.

The device for proposed therapy may include a bipolar electrode system, where electrodes alternate between active and return function and where the thermal gradient beneath electrodes is almost the same during treatment. However, a group of bipolar electrodes may be used as well. Alternatively, a monopolar electrode system may be used. With the monopolar arrangement, the return electrode has a sufficiently large area in comparison to active electrode. The return electrode is in contact with skin of the patient and may by positioned relatively farther from the active electrode. A unipolar electrode may also optionally be used. Both capacitive and resistive electrodes may be used.

In order to increase deep tissue heating by the electromagnetic field, the distance between electrodes may be varied; the electromagnetic field may be phase shifted or modulated; or an external magnetic field may be applied.

According to another embodiment, the electromagnetic field may be represented by near infrared waves generated by at least one laser diode module or LED approximately in the range from 600 nm to 1200 nm, more preferably from 630 nm to 990 nm. The emission output power of the laser diode module or LED are in the range from about 10 mW to about 10 W.

Energy flux density of the electromagnetic field is preferably in the range between 0.01 mW·mm$^{-2}$ and 10 000 mW·mm$^{-2}$, more preferably in the range between 0.1 mW·mm$^{-2}$ and 5 000 mW·mm$^{-2}$, most preferably in the range between 0.5 mW·mm$^{-2}$ and 1 000 mW·mm$^{-2}$.

The sum of energy flux density of the shock wave and electromagnetic field applied to the patient simultaneously, successively or in overlap should be preferably above 0.1 mW·mm$^{-2}$, more preferably above 1 mW·mm$^{-2}$, most preferably above 5 mW·mm$^{-2}$, generally up to a maximum of 100, 500 or 1000 mW·mm$^{-2}$.

Figure 2:
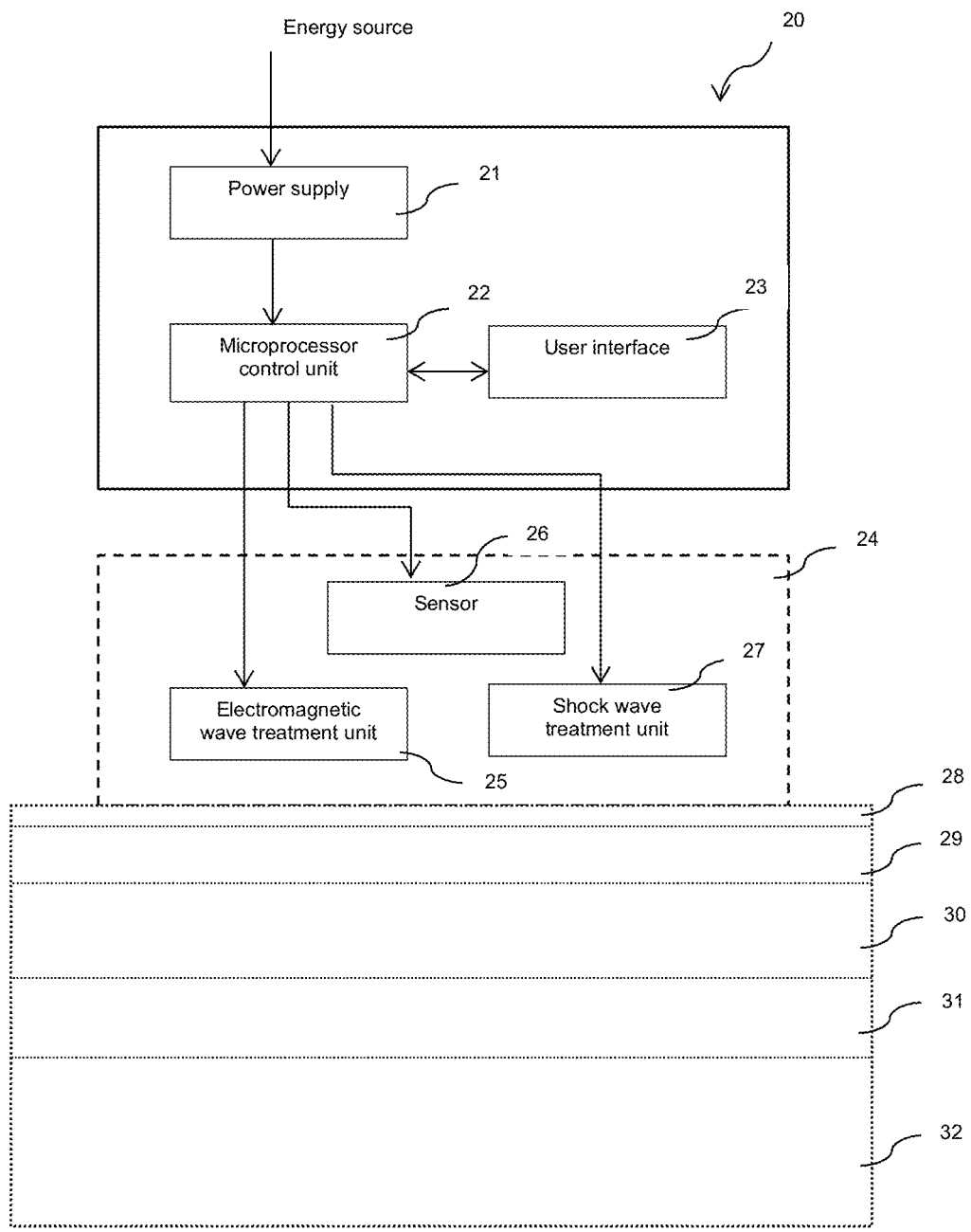
FIG. 2 is a schematic example of positioning of the system for skin treatment

FIG. 2 shows schematic example of positioning of the system for skin treatment. The system for skin treatment 20 applies a combination of electromagnetic and shock wave energy into the soft tissue. The system may include a power supply 21 connected to an energy source. The system for skin treatment 20 includes at least one applicator 24 which may be placed inside a case or may be separated from the system for skin treatment 20 and connected by a cable. The microprocessor control unit 22 with user interface 23 provides communication between the electromagnetic field treatment unit 25 and shock wave treatment unit 27. User interface 23 allows setting up the treatment parameters and also may provide the operator various treatment information. The electromagnetic field treatment unit 25 and shock wave treatment unit 27 may be placed in at least one applicator 24. However the treatment units may also have separate applicators. The applicator 24 may preferably contain a sensor unit 26

The sensor unit 26 may contain one or more sensors for sensing temperature, resistance, contact with skin or force applied to skin.

The temperature sensor measures and monitors the temperature of the treated tissue. Temperature can be analyzed by a microprocessor control unit 22. The temperature sensor may be a contact sensor, contactless sensor (e.g. infrared temperature sensor) or invasive sensor (e.g. a thermocouple) for precise temperature measuring of deep layers of soft tissue. The microprocessor control unit 22 may also use algorithms to calculate the deep or upper-most. A temperatures feedback system may control the temperature and based on set/pre-set limits, alert the operator in human perceptible form e.g. on the user interface 23. In a limit temperature condition, the device may be configured to adjust output power, activate cooling or stop the therapy.

A resistance sensor may measure the skin resistance, since it may vary for different patients, as well as the humidity, wetness and sweat may influence the resistance and therefore the behavior of the skin to electromagnetic field. Based on the measured skin resistance, the skin impedance may also be calculated.

The contact and/or force applied by the applicator on the skin surface may be measured piezoresistively, mechanically, optically, electrically, electromagnetically or magnetically. The measured information from the contact and/or force sensor may influence the start of the therapy or generation of electromagnetic or mechanic field by treatment units.

The system for skin treatment 20 generates electromagnetic waves and shock waves enabling improvement of the soft tissue, mainly connective tissue in the skin area. The connective tissue in the skin area contains layer epidermis 28 and dermis 29; white adipose tissue in hypodermis 30 and peritoneal cavity 32. The other soft tissue below the skin area e.g. muscular tissue 31 remains untreated and unharmed. The therapy may stimulate the blood circulation or may also create micro-disruptions of treated tissue, and/or create movement, rotation or polarization of particles by induced current and/or magnetic field which increase the temperature of treated tissue. The combined therapy may result in increased cell membrane permeability, which may result in increased liquefying of fat and/or lipolysis. Combination of both therapies highly reduces the risk of adipocytes inflammation.

Without being bound to the theory, it is believed that the shock wave may increase the penetration depth and enable remodeling of the visceral white adipose tissue which is located in the peritoneal cavity 32. The shock waves, in combination with electromagnetic field, may result in reduction of visceral fat cells. Therefore the overall number and/or volume of SWAT and/or VWAT may be reduced. Temperature of the treated tissue during the therapy may be increased to about 32-48° C.

Also neovascularization may be induced based on increased angiogenic grow factors VEGF, and also PCNA, NOS etc. Improvement of microvascular network may also result in better lipid metabolism functionality.

Another soft tissue improvement is in the field of tissue elasticity. The micro-disruptions also lead to improved tissue regeneration and in combination with electromagnetic field therapy induces neocollagenesis, neoelastogenesis and improvement of tissue elasticity. Although neocollagenesis is normally induced at higher temperatures than 32-48° C., the combination of shock wave and electromagnetic field enables improved results at temperatures in this range, resulting in less stress of the tissue.

The shock waves also have analgesic and myorelaxative effects which increase the comfort of therapy.

In another embodiment, the method and device may include a suction unit. The suction unit provides a vacuum or negative pressure on the treated skin. The suction unit may improve the contact shock wave treatment unit and/or electromagnetic field treatment unit with the skin surface and ensure better therapy.

The arrangement of shock wave treatment unit 27 and electromagnetic wave treatment unit 25 may be in one or more separate applicators 24. Where one applicator is used, the applicator 24 may contain one treatment electrode designed for transmission of mechanical waves and electromagnetic waves into the soft tissue. However, the shock wave treatment unit 27 and electromagnetic wave treatment unit 25 may be designed with separate wave outputs organized in concentric, axial symmetrical or non-symmetrical ways.

The methods and device described may provide an overall solution for soft tissue treatment, mainly in skin region including reduction in size and or volume of fat cells. The therapy also enables improvement of cellulite. The cellulite may be treated preferably without shrinkage of collagen fibers, since the triple helix structure is not denatured. Instead the method and system cause only micro-disruption at increased temperatures in the range 32-48° C. which increases the repair processes and collagen deposition.

Briefly stated, a method for soft tissue treatment of a patient includes positioning an applicator adjacent to the soft tissue of the patient; transmitting shock waves into the soft tissue of the patient causing mechanical stimulation of the soft tissue of the patient; transmitting electromagnetic waves from the applicator into the soft tissue with the electromagnetic waves heating the soft tissue; and remodeling soft tissues via the combination of shock waves and electromagnetic waves. The method may remodel the soft tissue and cause reduction of the VWAT and/or the SWAT; reduction in the number of adipose cells; reduction in the volume of adipose cells; and/or improve connective tissue elasticity or cellulite appearance. The method may also improve elasticity of fibrous septae connecting the dermis to underlying fascia.

Thus, novel apparatus and methods have been shown and described. Various changes and substitutions may of course be made without departing from the spirit and scope of the invention. The invention, therefore, should not be limited except by the following claims and their equivalents.

The invention claimed is:

1. A method for treatment of subcutaneous white adipose tissue of a patient comprising:
    positioning an applicator adjacent to subcutaneous white adipose tissue of the patient;
    transmitting radial/non-focused shock waves into the subcutaneous white adipose tissue of the patient causing mechanical stimulation of the subcutaneous white adipose tissue of the patient;
    transmitting electromagnetic waves from the applicator into the subcutaneous white adipose tissue with the electromagnetic waves heating the subcutaneous white adipose tissue;
    remodeling the subcutaneous white adipose tissue via the combination of shock waves and electromagnetic waves;
    where the shock waves frequency is in the range of 0.1 Hz to 100 Hz; and
    where sum of energy flux of the shock waves and electromagnetic field is in the range between 0.1 mW·mm$^{-2}$ and 1000 mW·mm$^{-2}$.

2. The method of claim 1 wherein the temperature of the subcutaneous white adipose tissue is increased to about 32-48° C.

3. The method of claim 2 wherein the electromagnetic field frequency is in the range of 0.1 MHz to 28 MHz.

4. The method of claim 3 where the shock waves are ballistic shock waves.

5. The method of claim 4 where the shock waves have a positive peak pressure greater than 15 MPa.

6. The method of claim 5 where a force applied by the applicator on the skin surface is measured by a sensor.

7. The method of claim 5 wherein a positive peak pressure of the shock waves is greater than a negative peak pressure of the shock waves.

8. A method for treatment of visceral white adipose tissue of a patient comprising:
    positioning an applicator adjacent to visceral white adipose tissue of the patient;
    transmitting radial/non-focused shock waves into the visceral white adipose tissue of the patient causing mechanical stimulation of the visceral white adipose tissue of the patient;
    transmitting electromagnetic waves from the applicator into the visceral white adipose tissue with the electromagnetic waves heating the visceral white adipose tissue; and
    remodeling the visceral white adipose tissue via the combination of shock waves and electromagnetic waves;
    wherein the shock waves frequency is in the range of 0.1 Hz to 100 Hz; and
    wherein the temperature of the subcutaneous visceral adipose tissue is increased to about 32-48° C.

9. The method of claim 8 where sum of energy flux of the shock wave and electromagnetic field is in the range of 0.1 mW·mm$^{-2}$ and 1000 mW·mm$^{-2}$.

10. The method of claim 9 wherein the electromagnetic field frequency is in the range of 0.1 MHz to 28 MHz.

11. The method of claim 9 where the shock waves are ballistic shock waves.

12. The method of claim 11 where the shock waves have a positive peak pressure greater than 15 MPa and up to 150 MPa.

13. The method of claim 12 wherein a force applied by the applicator on the skin surface is measured by a sensor.

14. The method of claim 13 where the combination of electromagnetic waves and shock waves reduces risk of adipocyte inflammation.

15. A method for treating cellulite comprising:
    positioning an applicator adjacent to cellulite tissue of the patient;
    transmitting radial/non-focused shock waves into the cellulite tissue of the patient causing mechanical stimulation of the cellulite tissue of the patient;
    transmitting electromagnetic waves from the applicator into the cellulite tissue with the electromagnetic waves heating the cellulite tissue;
    remodeling the cellulite tissue via the combination of shock waves and electromagnetic waves; and
    wherein the shock wave frequency is in the range of 0.1 Hz to 100 Hz; and
    wherein the temperature of the cellulite tissue is increased to about 32-48° C.

16. The method of claim 15 where sum of energy flux of the shock wave and electromagnetic field is in the range of 0.1 mW·mm$^{-2}$ and 1000 mW·mm$^{-2}$.

17. The method of claim 16 wherein the electromagnetic field frequency is in the range of 0.1 MHz to 28 MHz.

18. The method of claim 17 wherein the shock waves are ballistic shock waves.

19. The method of claim 18 wherein the shock waves have a positive peak pressure greater than 15 MPa.

20. The method of claim 19 further comprising sensing the applicator making contact with a skin surface via a sensor.

21. The method of claim 20 wherein a force applied by the applicator on the skin surface is measured by the sensor.

22. The method of claim 18 wherein a positive peak pressure of the shock waves is greater than a negative peak pressure of the shock waves.

23. A method for treatment of dermal tissue of a patient comprising:
    positioning an applicator adjacent to dermal tissue of the patient;
    transmitting radial/non-focused ballistic shock waves into the dermal tissue of the patient causing mechanical stimulation of the dermal tissue of the patient;
    transmitting radiofrequency waves from the applicator into the adipose tissue with the radiofrequency waves heating the dermal tissue wherein the temperature of the adipose tissue is increased to about 32-48° C.;
    remodeling the dermal tissue via the combination of the shock waves and the radiofrequency waves; and
    where the shock waves frequency is in the range of 0.1 Hz to 100 Hz; and
    where sum of energy flux of the shock waves and electromagnetic field is in the range between 0.1 mW·mm$^{-2}$ and 1000 mW·mm$^{-2}$.

24. The method of claim 23 wherein the temperature of the adipose tissue is increased to about 32-48° C.

25. The method of claim 24 wherein the electromagnetic field frequency is in the range of 0.1 MHz to 28 MHz.

26. The method of claim 25 where the shock waves are ballistic shock waves.

27. The method of claim 26 where the shock waves have a positive peak pressure of greater than 15 MPa.

28. The method of claim 27 further comprising sensing the applicator making contact with a skin surface via a sensor.

29. The method of claim 28 wherein a force applied by the applicator on the skin surface is sensed by the sensor.

30. The method of claim 29 where the pulse duration of the shock waves is in the range of 100 ns to 99 μs.

* * * * *